United States Patent [19]

Chao et al.

[11] 4,178,391

[45] Dec. 11, 1979

[54] PROCESS FOR IMPROVING THE FUNCTIONAL PROPERTIES OF PROTEIN MATERIAL

[75] Inventors: Kwei C. Chao, Naperville, Ill.; John A. Ridgway, Jr., LaPorte, Ind.; Philip G. Schnell, Wheaton; Jacqueline H. Pearce, Lisle, both of Ill.

[73] Assignee: Standard Oil Company a corporation of Indiana, Chicago, Ill.

[21] Appl. No.: 861,458

[22] Filed: Dec. 16, 1977

Related U.S. Application Data

[63] Continuation-in-part of Ser. No. 691,770, Jun. 1, 1976, abandoned.

[51] Int. Cl.$^2$ ............................................... A23J 3/00
[52] U.S. Cl. ........................................ 426/61; 426/62; 426/583; 426/656; 426/653
[58] Field of Search .................... 426/60, 61, 62, 583, 426/656, 657, 653

[56] References Cited

U.S. PATENT DOCUMENTS

| | | | |
|---|---|---|---|
| 3,642,492 | 2/1972 | Arndt | 426/656 X |
| 3,873,751 | 3/1975 | Arndt | 426/583 |
| 3,912,819 | 10/1975 | Chandler et al. | 426/60 X |
| 3,917,878 | 11/1975 | Kumar et al. | 426/656 |
| 3,943,264 | 3/1976 | Davis | 426/583 X |
| 3,947,605 | 3/1976 | Chao | 426/60 X |
| 3,966,992 | 6/1976 | Banks et al. | 426/583 |
| 4,036,999 | 7/1977 | Grindstaff | 426/583 X |
| 4,041,187 | 8/1977 | Nelson et al. | 426/656 X |

FOREIGN PATENT DOCUMENTS

1481417 7/1977 United Kingdom.

*Primary Examiner*—Raymond N. Jones
*Assistant Examiner*—Esther M. Kepplinger
*Attorney, Agent, or Firm*—Gregory E. Croft; Arthur G. Gilkes; William T. McClain

[57] ABSTRACT

Protein-containing materials are treated at specified temperature and pH conditions for a suitable length of time to yield products which replace material such as egg solids and nonfat dry milk.

23 Claims, No Drawings

PROCESS FOR IMPROVING THE FUNCTIONAL PROPERTIES OF PROTEIN MATERIAL

This application is a continuation-in-part of copending application Ser. No. 691,770, filed June 1, 1976 now abandoned.

BACKGROUND OF THE INVENTION

This invention relates generally to the improvement of the functional properties or proteinaceous materials such as single-cell proteins, plant proteins, whey solids, and mixtures thereof. More precisely, this invention involves subjecting the protein-containing material to a controlled pH, temperature, and time treatment which results in the improvement of the functional properties. For purposes of this invention, yeasts are considered as being separate from the plant proteins and are included within the single-cell protein category.

In recent years much attention has been directed toward the development of protein materials which can be incorporated in foods or food additives suitable for human consumption. Looking at plant proteins available today, it has been observed that these materials contribute to the off flavor, after flavor, undesirable color, unbalanced nutrients, or unacceptability in various food products. Similarly, untreated single-cell protein materials have been observed to have adverse effects on dough property and the bread quality. As would be expected, mixtures of single-cell and plant protein material have undesirable functional characteristics from each of the separate protein source materials.

The use of single-cell materials as a source for protein and the problems associated therewith can be better understood by looking more closely at a member selected from this class of materials, such as yeast cells. Yeast cells have the characteristic flavor and aroma which are affected to some extent by the growth conditions and the after-harvest processing conditions. They have a complicated organoleptic profile which consists of both pleasing and unpleasant flavors. One of the reasons limiting the use of yeast materials in food systems is the deleterious effect of its "yeasty" flavor. Where it is desirable to use yeast material at high levels for protein enrichment, a product of bland taste is preferred. Although the majority of yeasty flavor components can be easily removed from the yeast cells by a hot water extraction method, the use of such a process results in the loss of 15 to 20% in product yield. Furthermore, the extracted cells will retain some bitter, beany, and metallic off-taste. The loss in yield may be compensated by the value of the meat-flavored extract as a by-product, but the poor flavor of the cell product would need definite improvement. In addition, the hot water-extracted yeast cells contain about 0.6 to 1.0% phosphorus and 0.01 to 0.02% calcium. In order to achieve a nutritional balance of the calcium-phosphorus ratio for a food system in which such yeast is used, additional calcium may be necessary.

Particular attention has been directed to the use of single-cell protein materials, such as yeast, as a replacer for egg solids and nonfat dry milk (NFDM). For example, in the bakery industry, 2 to 3% nonfat dry milk is normally used as an additive to improve the physical and nutritional quality of bread. However, in view of the increasing cost and decreasing availability of milk, many bakers are looking for a substitute. Although certan products derived from soy protein have gained some acceptance, the active search by food technologists for a suitable substitute for milk in food products continues.

In this regard we have observed that during the fermentation and baking of bread dough, the wheat protein (gluten) forms the structure to hold the small bubbles of gas which are generated. This functional property permits the bread to rise and results in the production of bread having good volume and fine crumb structure. However, when untreated single-cell materials, such as dried inactive yeast, are added to bread dough to replace 2% nonfat dry milk, undesirable changes are observed in the property of the dough which adversely affect the bread quality. Typically, dough which contains unreacted yeast is soft, stringy, sticky and moist to the extent of rendering it difficult to handle. In fact, the dough has poor machinability characteristics which are detectable from the mixing to the final proofing stage. The inferior property of the dough is probably due to the poor water absorption and the strong reducing property of the thiol group in the yeast cell which damages the gluten structure. We have now found that materials such as yeast, plant, whey solids and combinations thereof can be treated according to the process of this invention to yield products highly suitable for replacing egg solids and nonfat dry milk. During the treatment of the yeast cells in accordance with the present process, several things happen which improve the functional property of the cell. The yeasty off-flavor is greatly reduced and cell material becomes significantly bland in taste by heating the yeast cells under controlled pH reaction conditions. A large amount of buffering materials are released from the cell by the heating process, which increase the buffering capacity of the food system when they are incorporated as dry yeast cell material. The saponification of lipid material gives rise to a soap material which is a good emulsifier. Also, heating under alkaline pH conditions will enhance the auto-oxidation of the thiol groups and the water holding capacity.

SUMMARY OF THE INVENTION

According to this invention, there is provided a process for treating protein materials such as single-cell protein material, plant protein material, whey solids, or mixtures thereof in a manner whereby the color, flavor, nutritional value, and functional properties of said materials are improved for food use. Where a mixture is being used, the amount of the single-cell protein component can vary from about 1 to about 99 percent. Moreover, the aqueous slurry can be treated with a basic compound, preferably a calcium compound, and fortified with an amino acid such as methionine or cystine. An aqueous slurry of the protein material is prepared and heated to a temperature of from about 75° to about 100° C. and the pH of the heated protein material is adjusted within the range of about 6.6 to about 8.0, preferably about 7.2 to about 7.6, by adding a pH adjusting compound. The pH adjusting compound can be selected from among the group consisting of anhydrous ammonia, ammonium hydroxide, calcium hydroxide, sodium hydroxide, sodium bicarbonate, calcium sulfate, potassium carbonate, potassium bicarbonate, calcium carbonate, sodium carbonate, potassium hydroxide, magnesium hydroxide, and mixtures thereof, especially mixtures of calcium hydroxide and calcium carbonate or calcium sulfate. Additionally, the pH adjustment can be accompanied by the agitation and oxidation of the single-cell protein. The pH adjusted solution is maintained at temperature for a period of about 1 to about 120 minutes and then dried. Alternatively, as illustrated in FIG. 2, the pH adjusted slurry is separated into (1) a protein extract and (2) a base-treated protein material, particularly with a basic calcium compound, wherein the base-treated protein material is removed, water washed and dried with or without the addition of amino acids. The protein extract can be heated to an increased concentration and dried for use as a seasoning ingredient.

By the practice of this invention one can prepare a proteinaceous material having improved functional properties.

DESCRIPTION OF THE PREFERRED EMBODIMENTS

The process of this invention provides a method for improving the functional properties of single-cell protein, plant protein, whey solids, or mixtures thereof.

It is believed that any microbial cell material, plant protein, whey solution, or mixtures thereof can be treated according to the process of this invention, although this invention is particularly suited for processing yeasts such as *Candida utilis*. In a fully integrated, continuous system, microbial cells are conveniently grown in a first fermenting stage where oxygen and a suitable substrate, such as liquid or gaseous hydrocarbons or oxygenated hydrocarbons such as carbohydrates or alcohols, together with a nutrient solution containing minerals are fed to a stirred reactor containing the microorganisms. In a continuous fermentation at steady state, a portion of the reacting mixture is withdrawn at a constant concentration of microorganisms. The concentration of the cells is typically increased by mechanical or evaporative means. As the microorganism concentration increases, a portion of the reacting mixture is withdrawn from the stirred reactor and the microorganisms are separated from the withdrawn reaction mixture.

By way of illustration, bacteria such as those listed in TABLE I, yeasts such as those listed in TABLE II, and fungi such as those listed in TABLE III are suitable single-cell protein materials for use as starting materials in the practice of this invention.

TABLE I—Suitable Bacteria

Acetobacter sp.
Arthrobacter sp.
*Bacillus subtilis*
Corynebacterium sp.
Micrococcus sp.
Pseudomonas sp.

TABLE II—Suitable Yeasts

*Candida curvata*
*Candida lipolytica*
*Candida pulcherima*
*Candida utilis*
*Hansenula anomala*
*Pichia farinosa*
*Oidium lactis*
*Saccharomyces carlsbergensis*
*Saccharomyces cerevisiae*
*Saccharomyces fragilis*
*Trichosporon cutaneum*

TABLE III—Suitable Fungi

*Aspergillus niger*
*Aspergillus glaucus*
*Aspergillus oryzae*
*Aspergillus terreus*
*Aspergillus itaconicus*
*Penicillium notatum*
*Penicillium chrysogenum*
*Penicillium glaucum*
*Penicillium griseofulyum*

*Candida utilis, Saccharomyces cerevisiae, Saccharomyces fragilis*, or *Saccharomyces carlsbergensis* are suggested single-cell starting component materials for the process of this invention, because each is approved by the U.S. Food and Drug Administration as suitable for use in food products.

The plant protein material is advantageously selected from oil seed protein materials such as soy flour, defatted soy flour, soy flakes, soy protein isolates and concentrates, cotton seed flour, cotton seed protein isolates and concentrates, peanut flour, peanut protein isolates and concentrates, sesame seed flour, sesame seed protein isolates and concentrates, corn grits, corn protein isolates and concentrates, gluten, cereal protein isolates and concentrates, rapeseed flour and rapeseed protein isolates and concentrates.

The whey material can be whey solids in the form of an aqueous solution, condensed suspension of crystals, or a dried powder. The whey may be derived from the processing of Cheddar, Brick, Edam, Parmesan, Gouda, Emmenthaler (Swiss), or other cheeses.

The following schematic diagrams (FIGS. 1 to 3), TABLES IV to VIII, and EXAMPLES I to XI are illustrative, without implied limitation, of this invention.

EXAMPLE I

The following three testing samples were prepared from a 10% solids yeast cell slurry under the condition as described in the diagram shown in FIG. 1.

(a) untreated spray-dried cells
(b) heated at 95° C. and pH 5.9 for 30 minutes
(c) heated 95° C. and pH 7.5 (0.88 g. NaOH/100 g dry cell) for 30 minutes.

The samples were submitted for bread-baking test. The results are summarized in TABLE IV. The best result, as it is comparable to that of NFDM, is from the sample prepared by heating at pH 7.5. The most significant improvement is in its dough property. The baking test results indicate the importance of the pH effect during the heat treatment.

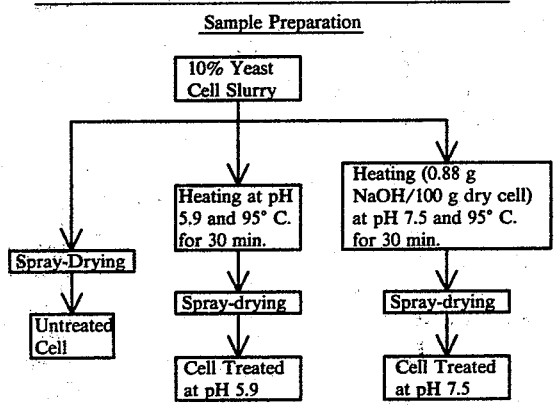

FIGURE 1

COMPARATIVE PROCESSES FOR PREPARING A YEAST, PLANT OR YEAST-PLANT PRODUCT TO BE USED AS A REPLACEMENT FOR NONFAT DRY MILK

TABLE IV

Performance in Dough Handling

| As Additive (2%) | Characteristics |
|---|---|
| NFDM | Good in mixer, rounding, and moulder. Normal into oven. |
| Untreated Cells | Not tolerant to mixer. Sticky and stringy off mixer. Recovered for rounding. Flat into oven. |
| Cells treated* at pH 5.9 | The same as that of untreated cells. |
| Cells treated* at pH 7.5 | Equal to that of NFDM. |

*Heating at 95° C. for 30 minutes under open air with constant agitation.

As previously mentioned, untreated yeast cells have a high content of thiol groups. Soluble compounds such as gluthathione and cystine, as well as the thiol group in the water soluble protein are active materials which will weaken the gluten structure by the sulfhydryl-disulfide interchange reaction during the dough mixing and proofing. The thiol group is readily oxidized, especially under heating at increased pH with trace amounts of metal ions. Experimental results in TABLE V illustrates the effect of heating at increased pH in order to achieve the auto-oxidation of thiol in Candida utilis cells. Two things are indicated: (1) the thiol may be oxidized to various compounds beyond the less oxidized form of disulfide as indicated by the data showing that 61% of the total thiol in yeast is lost through the auto-oxidation from heating at the pH of 7.5, while only 30.5% is lost at the pH of 5.9, and (2) almost all of the remaining thiol groups are in reactive form which apparently represents the thiol groups of insoluble protein existing intracellularly and unreacted. These residual thiol groups in the treated yeast cell are most probably inactive during bread-making when the cells are mixed into the dough. Only soluble thiol compounds such as gultathione and cystine will affect the gluten structure.

TABLE V

Effect of Heating At Increased pH To The Auto-oxidation of Thiol in Yeast Cells[1]

| Cell Treatment | Reactive SH (milli-equivalents/gram) | Total SH (milli-equivalents gram) | SH Loss % |
|---|---|---|---|
| Untreated | 21.6 | 30.7 | 0 |
| pH 5.9[2] | 12.9 | 21.3 | 30.5 |
| pH 7.5[2] | 10.4 | 12.0 | 61.0 |

[1]Candida utilis ATCC 9256. Continuous culture grown on ethanol at $O_2$ - limiting condition.
[2]Heating at 95° C. for 30 minutes under open air with constant agitation.
[3]Analyzed by the method of C. C. Tsen and J. A. Anderson ("Determination of Sulfhydryl and Disulfide Groups in Flour and Their Relation to Wheat Quality" Cereal Chem. 40: 314–323, 1963).

EXAMPLE II

A sample was prepared by digesting a 10% torula yeast cell slurry at 75° C. and pH 7.0 for one hour. The baking test results as summarized below indicate that its quality is comparable to NFDM as an additive to bread-baking.

| Sample | Bread Score | Dough Property |
|---|---|---|
| Untreated cell | 83 | sticky and wet |
| Treated cell | 97 | normal |
| NFDM | 98 | normal |

EXAMPLE III

The experiment of calcium treatment was carried out as outlined in FIG. 2.

Aliquots of 200 ml of yeast cream which contains 10% cell by weight, are dispensed into each of the 400 ml beakers, with or without the addition of various calcium compounds as listed in TABLE VI. The amount of calcium added is calculated from the basis of 2% phosphorus in the aliquot of cell material and of a ratio of calcium to phosphorus of one.

The slurry was heated rapidly to 80° C. by a submerged steam coil under constant stirring. At the end of 10 minutes' cooking period, the heated material was quickly cooled down to room temperature by circulating the cooling water through the coil. The pH of the treated slurry was measured and adjusted, as necessary, to a value of 6.7. The cell material was separated, washed, and dried. The yeast extract was directly subjected to sensory test without further treatment. The results of the treatment using various calcium compounds as compared to the control are summarized in TABLES VI, VII, and VIII.

The experiment results indicate that:

1. A bland-taste cell material is obtainable by cooking the yeast with $CaCO_3$, where the pH is close to the neutral. Bad flavors are produced when the cells are reacted with $Ca(OH)_2$ at an alkaline pH, or with $CaCl_2$ at an acidic pH.

2. The yeast extracts obtained from the treatment with various calcium compound are significantly different in their color, odor, and tasteから that of the control. The best choice is still the one from the $CaCO_3$ treatment.

3. Tasting of the unfractionated products prepared from the above calcium treatments indicated that calcium carbonate ($CaCO_3$) treated material gave the best flavor. This means that a control of pH close to 7 is very critical to the flavor of the treated yeast products.

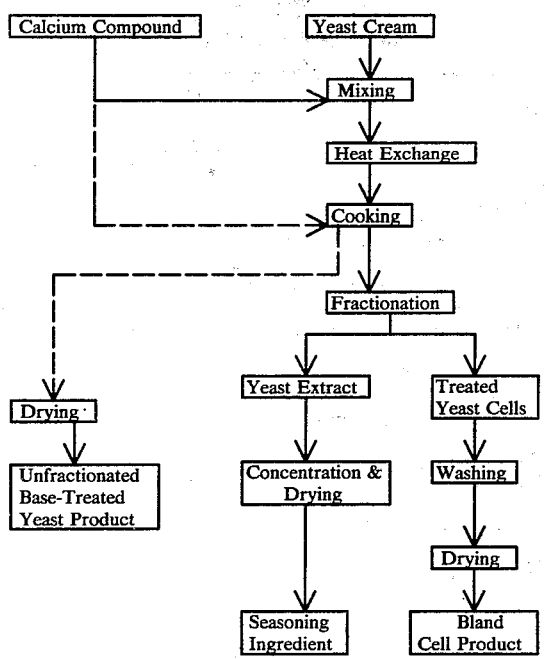

FIGURE 2
Process Flowsheet

TABLE VI

The Calcium-Treated Yeast Cells[1]

| Treatment[2] | pH[3] | Yield[4] | Color | Flavor[5] |
|---|---|---|---|---|
| Control | 6.2 | 84.3 | Whitish | Slightly bitter |
| 5.0% CaCO3 | 6.7 | 85.0 | Whitish | Bland |
| 3.7% Ca(OH)2 | 9.2 | 80.0 | Cream | Fairly bitter |
| 5.5% CaCl2 | 5.6 | 84.4 | Pinkish | Fairly bitter and astringent |

[1] Cooked at 80° C. for 10 minutes, washed, and dried
[2] The weight of calcium compound added is based on the dry weight of yeast cell which contains 2% P. The ratio of Ca/P is about 1.
[3] Unadjusted pH reading of the cooked slurry.
[4] After the pH of the slurry is adjusted to 6.7.
[5] Sensory test of a 5% suspension in water.

TABLE VII

The Yeast Extract From Various Calcium Treatment[1]

| Treatment[2] | Color | Color Intensity | Odor | Off-Flavor[3] |
|---|---|---|---|---|
| Control | Orange | +++ | Yeasty | Yeasty and beany |
| 5.0% CaCO3 | Yellowish | + | Hydrolyzate | Not detected |
| 3.7% Ca(OH)2 | Yellowish | + | Butyrous | Slightly beany |
| 5.5% CaCl2 | Orange-Yellowish | ++ | Yeasty | Slightly beany |

[1] Cooked at 80° C. for 10 minutes, separated from the cell material.
[2] The weight of calcium compound added is based on the dry weight of yeast cell.
[3] All of the samples give pleasing meaty flavor.

TABLE VIII

The Comparison of Egg Replacement Quality Between Calcium-treated and Untreated Blend Products In Yellow Cake Tests at 50% Egg Replacement Level

| Composition of Samples | Total Score* Yellow Cake | Expert Panel Comments |
|---|---|---|
| 80% Full Fat Soy Flour 20% inactive dry yeast (treated according to Example XI) | 90 | Bright color, finer crumb, egg taste, excellent body |
| 80% Full Fat Soy Flour 20% inactive dry yeast (untreated) | 84 | Dry testure, lacks flavor, soy taste, crumbles, burning aftertaste |
| 80% Defatted Soy Flour 20% inactive dry yeast (treated according to Exaple IX) | 96 | Excellent body, well defined crumb structure clean flavor |
| 80% Defatted Soy Flour 20% inactive dry yeast (untreated) | 74 | Poor body, good flavor, dry mouth-feel, open structure |
| 80% Triticale Flour 20% inactive dry yeast (treated according to Example X) | 94 | Excellent body, sweet egg flavor, good structure |
| 80% Triticale Flour 20% inactive dry yeast (untreated) | 90 | Gray color, gummy |

*Yellow cake score. Maximum possible score is 100 for best overall quality. The score for yellow cakes with 100% egg ranges from 94 to 96.

EXAMPLE IV

Yeast cream (containing 10–19% cell by weight) was heated to 80° C. The pH of the flowing stream was adjusted to within the range of 7.2 to 7.6 by blending with an aqueous suspension 1.7 weight percent calcium hydroxide (Ca(OH)2 and 8.5 weight percent calcium carbonate (CaCO3). The stream was held at temperature and pH for 2 to 4 minutes, then spray dried at rates up to 2,500 lb/hr. of dry product.

EXAMPLE V

Mixtures of yeast cream (10–19% cell by weight) and cheese whey (5–40% total solids by weight) were blended to levels of 27 to 47% whey (dry basis, by weight). The mixed stream was heated to 80° C., then treated with a combined aqueous suspension of calcium carbonate (CaCO3, 8.5% by weight) and calcium hydroxide (Ca(OH)2, 1.7% by weight) to effect a system pH within the range of 7.0 to 7.6. The process stream was held at 80° C. and 7.0–7.6 pH for 2–4 minutes, then spray dried at rates up to 80 lb/hr. of dry product output.

EXAMPLE VI

The process of Example V was repeated using sodium hydroxide (NaOH, 5.6% by weight) to adjust the pH to within the range of 6.8 to 7.0.

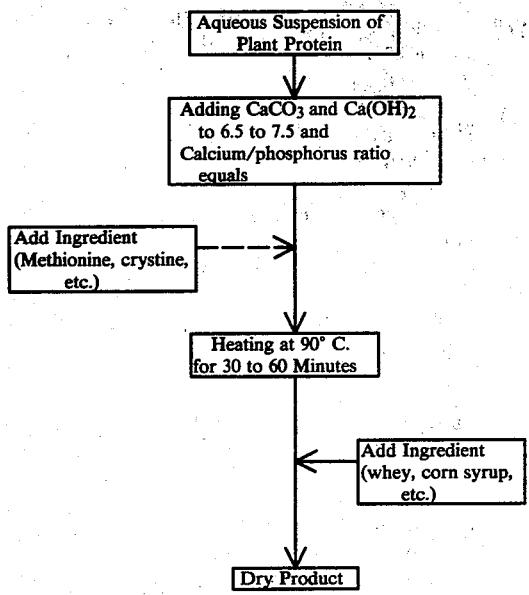

FIGURE 3
Production Of Modified Plant Protein

EXAMPLE VII

FIG. 3 outlines the process of the production of modified plant protein.

Calcium carbonate and calcium hydroxide is added to an aqueous soy protein solution until the pH is between 6.5 to 7.5. The aqueous suspension is heated 90° C. for 30 to 60 minutes and then dried.

EXAMPLE VIII

The same as Example VII except that methionine is added before the aqueous suspension is heated.

EXAMPLE IX

Twenty grams of Torutein (inactive dried yeast) was mixed with eighty grams of defatted soy flour. Eight hundred grams of water was added to form an aqueous mixture of Torutein and defatted soy flour. 1.7 grams of calcium hydroxide $(Ca(OH)_2)$ and 3.6 grams of calcium carbonate $(CaCO_3)$ was added to the aqueous mixture. The aqueous mixture was heated up to 190° F. over a period of 40 minutes, the temperature was maintained at 190° F. for 60 minutes, and allowed to cool to 70° F. over a period of 20 minutes. The cooled product was dried by freeze drying.

EXAMPLE X

The same as EXAMPLE IX except that triticale flour is used in place of defatted soy flour.

EXAMPLE XI

The same as EXAMPLE IX except that full fat soy flour is used in place of defatted soy flour.

The many uses and advantages of the treated products produced in accordance with this invention become apparent when it is realized that such products replace egg yolk and/or nonfat dry milk in an extensive array of food products. More particularly, it has been observed that the said products can replace nonfat dry milk in formulations which include such bakery goods as brownies, chocolate cake, chocolate krinkles, chocolate puddings, cinnamon rolls, cinnamon swirl loaf, coffee cake chemically leavened, coffee cake yeast raised, fudge, hamburger buns, high ratio yellow cake, nut fingers, pancakes, pecan loaf, pound cake, shortbread cookies, waffles, wheat flour tortillas, doughnut, yellow cake mix and related products.

We claim:

1. A process for improving the functional properties of protein-containing materials comprising the steps of:
   (a) preparing an aqueous slurry of a protein-containing material selected from the group consisting of
   (1) single-cell protein in the form of a cream, and
   (2) mixtures of single-cell protein cream with plant protein, whey solids, or both plant protein and whey solids, said mixtures containing from about 1 to about 99 weight percent of the single-cell protein component;
   (b) heating the aqueous slurry to a temperature of from about 75° to about 100° C.;
   (c) adjusting the pH of the heated slurry to within the range of about 6.6 to about 8.0 by adding a compound selected from the group consisting of anhydrous ammonia, ammonium hydroxide, calcium hydroxide, sodium hydroxide, sodium bicarbonate, calcium sulfate, potassium carbonate, potassium bicarbonate, calcium carbonate, sodium carbonate, potassium hydroxide, magnesium hyrdoxide and mixtures thereof;
   (d) maintaining the heated, pH-adjusted slurry at said conditions for a time period of from about 1 to about 10 minutes; and
   (e) drying the material from step (d).

2. The process of claim 1 wherein the protein-containing material in step (a) is a mixture of yeast and whey.

3. The process of claim 2 wherein the aqueous slurry is maintained at a pH of about 7.0–7.6 for from about 2 to about 4 minutes.

4. The process of claim 3 wherein the aqueous slurry is maintained at about 80° C.

5. The process of claim 4 wherein the pH is adjusted by adding calcium carbonate and calcium hydroxide.

6. The process of claim 1 wherein the protein-containing material in step (a) is a mixture of yeast cream and whey and the aqueous slurry is maintained at a pH in the range of 6.8 to 7.0.

7. The process of claim 6 wherein the aqueous slurry is heated to about 80° C. for from about 2 to about 4 minutes.

8. The process of claim 7 wherein the pH is adjusted by adding sodium hydroxide.

9. A process for improving the functional properties of a yeast material comprising the steps of:
   (a) preparing an aqueous slurry comprising a yeast cream material;
   (b) heating the slurry to a temperature of from about 75° to about 100° C.;
   (c) adjusting the pH of the slurry to from about 7.2 to about 7.6;
   (d) maintaining the heated, pH-adjusted slurry at said temperature and pH for from about 1 to about 10 minutes; and
   (e) drying the slurry.

10. The process of claim 9 wherein the yeast is *Candida utilis.*

11. The process of claim 9 wherein the slurry is heated to about 80° C.

12. The process of claim 9 wherein the pH is adjusted by the addition of calcium hydroxide and calcium carbonate.

13. The process of claim 9 wherein the slurry is maintained at said temperature and pH for about 2 minutes.

14. A process for improving the functional properties of Candida utilis yeast comprising the steps of:
 (a) treating a Candida utilis cream by maintaining the cream at a pH in the range of 7.2 to 7.6 and a temperature of about 80° C. for about 2 minutes, wherein the pH is adjusted by the addition of calcium hydroxide and calcium carbonate; and
 (b) drying the treated cream.

15. The product prepared by the process of claim 1.

16. The product prepared by the process of claim 9.

17. The product prepared by the process of claim 14.

18. A process for improving the functional properties of protein-containing materials comprising the steps of:
 (a) preparing an aqueous slurry of a protein-containing material selected from the group consisting of (1) single-cell protein in the form of a cream, and (2) mixtures of single-cell protein cream with plant protein, whey solids, or both plant protein and whey solids, said mixtures containing from about 1 to about 99 weight percent of the single-cell protein component;
 (b) heating the aqueous slurry to a temperature of from about 75° to about 100° C.;
 (c) adjusting the pH of the heated slurry to within the range of about 6.6 to about 8.0 by adding a compound selected from the group consisting of anhydrous ammonia, ammonium hydroxide, calcium hydroxide, sodium hydroxide, sodium bicarbonate, calcium sulfate, potassium carbonate, potassium bicarbonate, calcium carbonate, sodium carbonate, potassium hydroxide, magnesium hydroxide and mixtures thereof;
 (d) maintaining the heated, pH-adjusted slurry at said conditions for a time period of from about 1 to about 10 minutes; and
 (e) separating the slurry into a protein extract and a residual base-treated protein material; and
 (f) washing the residual protein material with water and drying same.

19. The process of claim 18 wherein the protein-containing material is a yeast.

20. The process of claim 19 wherein the yeast is Candida utilis.

21. A process for improving the functional properties of plant protein comprising the steps of:
 (a) preparing an aqueous suspension of the plant protein;
 (b) adjusting the pH of the solution to within the range of about 6.5 to about 7.5 by the addition of calcium carbonate, and calcium hydroxide;
 (c) heating the aqueous solution to a temperature of from about 75° to about 100° C.;
 (d) maintaining the solution at the abovesaid conditions for from about 30 to about 60 minutes; and
 (e) drying the material from step (d).

22. The process of claim 21 wherein the solution is heated to about 90° C.

23. The process of claim 22 wherein an amino acid such as methionine or cystine is added to the solution prior to heating.

UNITED STATES PATENT OFFICE
CERTIFICATE OF CORRECTION

Patent No. 4,178,391  Dated December 11, 1979

Inventor(s) Kwei C. Chao, John A. Ridgway, Jr., Philip G. Schnell and Jacqueline H. Pearce It is certified that error appears in the above-identified patent and that said Letters Patent are hereby corrected as shown below:

| Patent Column | Line | |
|---|---|---|
| 1 | 11 | "or" should read --of-- |
| 1 | 68 | "certan" should read --certain-- |
| 2 | 15 | "unreacted" should read --untreated-- |
| 7 | 67 | "testure" should read --texture-- |
| 9 | 11 | "equals" should read --equals 1-- |

Signed and Sealed this

Thirteenth Day of May 1980

[SEAL]

Attest:

SIDNEY A. DIAMOND

Attesting Officer  Commissioner of Patents and Trademarks